United States Patent
Shieh et al.

[11] Patent Number: 5,827,482
[45] Date of Patent: Oct. 27, 1998

[54] TRANSISTOR-BASED APPARATUS AND METHOD FOR MOLECULAR DETECTION AND FIELD ENHANCEMENT

[75] Inventors: Chan-Long Shieh, Paradise Valley, Ariz.; Donald E. Ackley, Cardiff, Calif.

[73] Assignee: Motorola Corporation, Schaumburg, Ill.

[21] Appl. No.: 699,757

[22] Filed: Aug. 20, 1996

[51] Int. Cl.$^6$ .......................... G01N 27/02; G01N 27/26; G01N 33/53; C12Q 1/68

[52] U.S. Cl. ........................ 422/82.02; 435/6; 435/7.1; 435/7.9; 435/4; 204/400; 204/403; 204/456; 436/518; 422/50; 422/68.1; 422/76; 422/82.01; 422/82.05

[58] Field of Search .......................... 435/6, 5, 7.1–7.9, 435/4, 817, 28, 285.2, 291, 174, 16; 204/153.1, 153.12, 400, 456, 403; 436/518, 149, 150, 806, 807, 524, 528, 527, 526; 422/50, 68.1, 76, 82.01, 82.02, 82.05; 530/300, 350, 333; 536/21, 37, 33, 23.1, 26.6; 424/94.1

[56] References Cited

U.S. PATENT DOCUMENTS

| | | |
|---|---|---|
| 4,490,216 | 12/1984 | McConnell ................................. 204/1 |
| 5,074,977 | 12/1991 | Cheung et al. ....................... 204/153.1 |
| 5,466,348 | 11/1995 | Holm Kennedy ................... 204/153.1 |
| 5,495,184 | 2/1996 | Des Rosiers et al. ..................... 326/73 |
| 5,556,752 | 9/1996 | Lockhart et al. ............................ 435/6 |
| 5,653,939 | 8/1997 | Hollis et al. .............................. 422/50 |

OTHER PUBLICATIONS

Storey, In ElectronicsL A Systems Apporpachpages 176–177, 1992.

*Primary Examiner*—W. Gary Jones
*Assistant Examiner*—Jeffrey Fredman
*Attorney, Agent, or Firm*—James E. Gauger; Douglas D. Fekete; Jonathan P. Meyer

[57] ABSTRACT

Binding of a molecule to a molecular receptor is sensed using a transistor having a gate located at a binding site. The channel conductance of the transistor is modified by a charge associated with the molecule when the molecule binds with the molecular receptor. A modified electrical characteristic of the transistor which results is sensed to sense the binding event. Electric field enhancement is provided by applying a voltage to the gate. A second sensing transistor can be coupled to the sensing transistor to form a differential pair. The differential pair allows for enhancing and sensing of differential binding events.

28 Claims, 4 Drawing Sheets

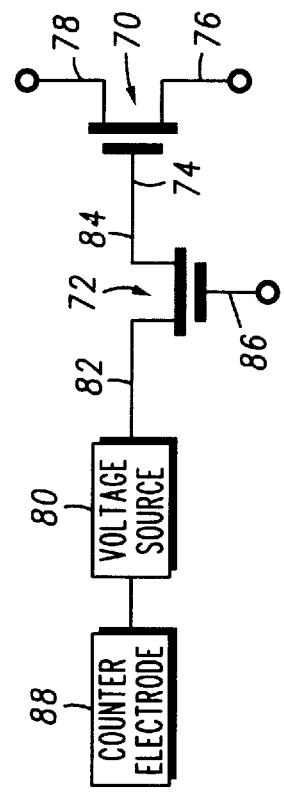
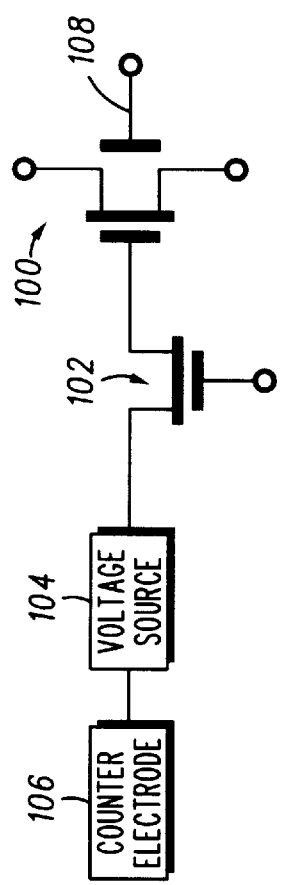
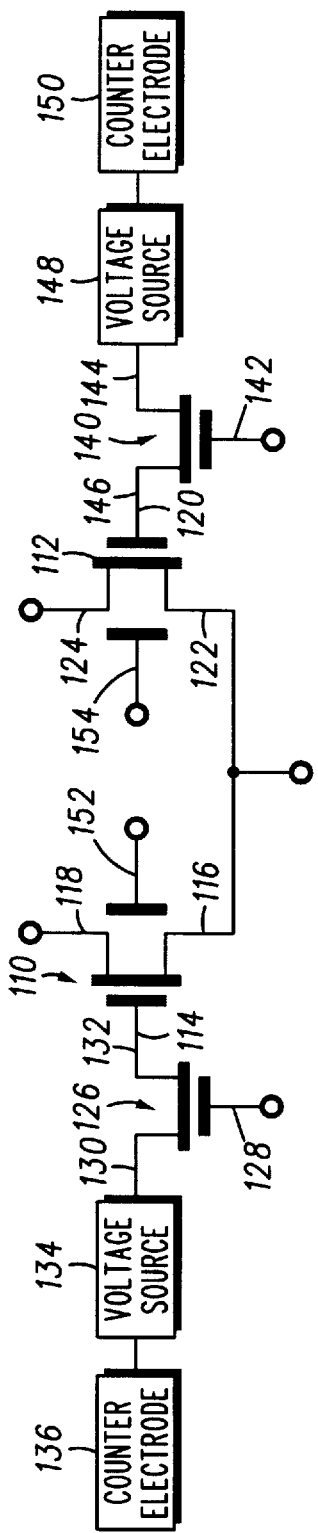

TRANSISTOR-BASED APPARATUS AND METHOD FOR MOLECULAR DETECTION AND FIELD ENHANCEMENT

FIELD OF THE INVENTION

The present invention relates to molecular detection devices.

BACKGROUND OF THE INVENTION

An increased effort has been directed toward the development of chips for molecular detection. In general, a molecular detection chip includes a substrate on which an array of binding sites is arranged. Each binding site (or hybridization site) has a respective molecular receptor which binds or hybridizes with a molecule having a predetermined structure. A sample solution is applied to the molecular detection chip, and molecules in the sample bind or hybridize at one or more of the binding sites. The particular binding sites at which hybridization occurs are detected, and one or more molecular structures within the sample are subsequently deduced.

Of great interest are molecular detection chips for gene sequencing. These chips, often referred to as DNA chips, utilize an array of selective binding sites each having respective single-stranded DNA probes. A sample of single-stranded DNA fragments, referred to as target DNA, is applied to the DNA chip. The DNA fragments attach to one or more of the DNA probes by a hybridization process. By detecting which DNA probes have a DNA fragment hybridized thereto, a sequence of nucleotide bases within the DNA fragment can be determined.

To hasten the hybridization process, a local concentration of target DNA can be increased at predetermined sites using electric field enhancements. Here, each site has an electrode associated therewith for selectively generating an electric field thereby. The electric field is generated by applying an electric potential between an electrode at the site and a counter electrode at a peripheral portion of the chip. To attract DNA fragments to the site, the polarity of the electric potential is selected to generate an electric field having a polarity opposite to the charge of the DNA fragments. To dehybridize the site, an electric field having the same polarity as the DNA fragments can be generated to repel the DNA fragments from the site.

Various approaches have been utilized to detect a hybridization event at a binding site. In one approach, a radioactive marker is attached to each of a plurality of molecules in the sample. The binding of a molecule to a molecular receptor is then detectable by detecting the radioactive marker.

Other approaches for detection utilize fluorescent labels, such as fluorophores which selectively illuminate when hybridization occurs. These fluorophores are illuminated by a pump light source external to the substrate. An external charge-coupled device (CCD) camera is utilized to detect fluorescence from the illuminated fluorophores.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

FIG. 5 is a schematic, block diagram of another embodiment of a molecular detection apparatus in accordance with the present invention;

FIG. 6 is a schematic, block diagram of yet another embodiment of a molecular detection apparatus;

FIG. 7 is a schematic, block diagram of a further embodiment of a molecular detection apparatus in accordance with the present invention;

DESCRIPTION OF THE PREFERRED EMBODIMENT

Embodiments of the present invention advantageously provide a molecular detection apparatus which detects the binding or hybridization of a molecule to a molecular receptor by sensing a charge associated with the molecule. A preferred embodiment utilizes a transistor having a gate which is situated at a binding site. The transistor is utilized both to detect binding events and to control hybridization and dehybridization at the binding site. A differential pair comprised of the transistor and a second transistor can be utilized for differential hybridization sensing. The differential pair is advantageous in eliminating a need for a counter electrode.

Figure 1:
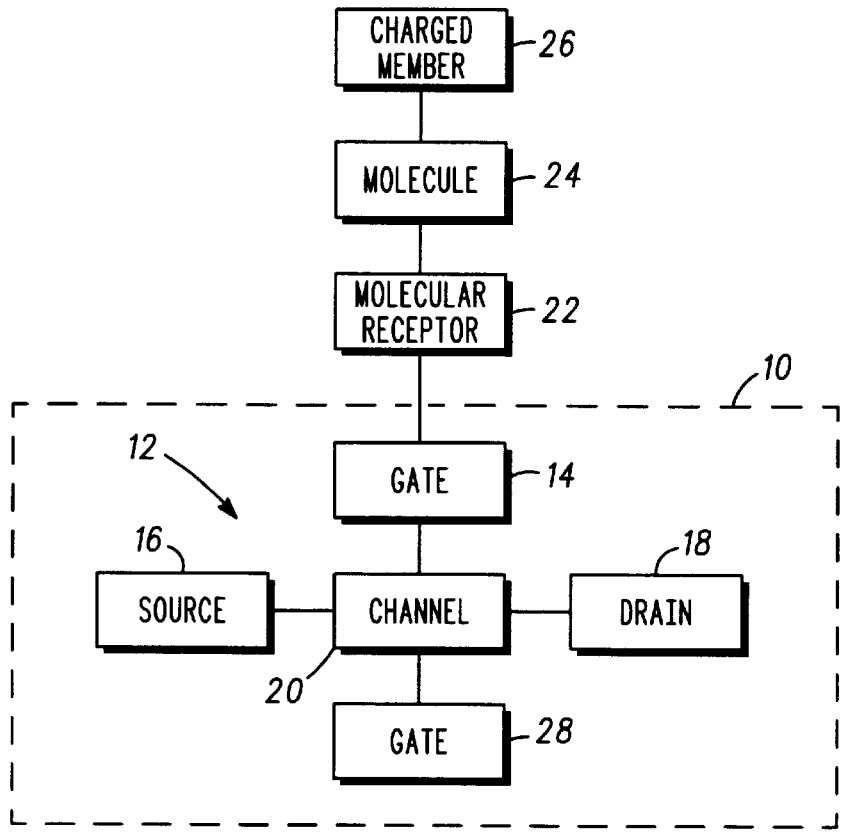
FIG. 1 is a block diagram of an embodiment of a molecular detection apparatus in accordance with the present invention.

FIG. 1 is a block diagram of an embodiment of a molecular detection apparatus 10 in accordance with the present invention. The molecular detection apparatus 10 includes a transistor 12 having a gate 14, a source 16, and a drain 18. The transistor 12 has a semiconductive channel 20 which electrically couples the source 16 to the drain 18. A conductance between the source 16 and the drain 18 is dependent upon a voltage or a charge applied to the gate 14.

The transistor 12 can be formed using various known technologies. Preferably, the transistor 12 is comprised of a thin-film transistor (TFT) or a field-effect transistor (FET) such as a metal-oxide semiconductor FET (MOSFET). In these cases, the semiconductive channel can be formed by a thin-film semiconductive layer or by bulk semiconductive material. The gate 14 can be either directly coupled to the semiconductive channel 20, or can be coupled to the semiconductive channel 20 by an insulator (not specifically illustrated).

The gate 14 is located at a binding site for receiving a molecular receptor 22. Preferably, the molecular receptor 22 is bound directly to the gate 14, in which case the gate 14 supports or defines the binding site. Here, the molecular receptor 22 can be bound to the gate 14 by a primer. More generally, the molecular receptor is electrically coupled,to the gate 14.

In general, the molecular receptor 22 is selected in dependence upon a molecule 24 which is to be detected. The molecular receptor 22 typically includes a biological or synthetic molecule that has a specific affinity to the molecule 24 to be detected. The molecular receptor 22 can include a chain of at least one nucleotide which hybridizes with a complementary chain of at least one nucleotide included in the molecule. Here, for example, the molecular receptor 22 can include a DNA probe for detecting a corresponding, complementary DNA sequence in the molecule 24. It is noted, however, that the scope of the invention is not limited to sensing the hybridization of DNA molecules. For example, embodiments of the present invention can be utilized to detect RNA hybridization and antibody-antigen binding events.

The conductance between the source 16 and the drain 18 is modified by a charge associated with the molecule 24 when the molecule 24 binds with the molecular receptor 22. The binding of the molecule 24 to the molecular receptor 22 is sensed by sensing a modified electrical characteristic of the transistor 12 which results from the charge associated with the molecule 24 being coupled to the gate 14.

The charge associated with the molecule 24 can be inherent in the molecule 24, such as the inherent charge in a DNA molecule. The charge associated with the molecule 24 may also result from a charged member 26 attached to the molecule 24. The charged member 26 is utilized to significantly enhance the magnitude of the charge associated with the molecule 24. If desired, substantially all of the charge associated with the molecule 24 can be provided by the charged member 26.

The charged member 26 can have the form of a charged bead attached to the molecule 24. The charged bead can have a spherical form, with a diameter on the order of 0.1 to 1.0 $\mu$m. If the molecule 24 includes a polymer chain, the charged member 26 can be attached to an end of the polymer chain using conventional primer techniques. This allows the charged member 26 to be attached to an end of a DNA molecule, for example.

In another embodiment, the charged member 26 is incorporated directly into the molecular structure of the molecule 24. For example, the charged member 26 can be incorporated directly into a DNA helix.

It is noted that the use of the charged member 26 is optional for the various embodiments of the present invention.

The transistor 12 can optionally include a second gate 28 which is utilized for sensing the modified electrical characteristic. Whereas the gate 14 is disposed on a first side of the semiconductive channel 20, the second gate 28 is disposed on a second side of the semiconductive channel 20. The second gate 28 can be utilized as a means of gain control and active feedback to improve the sensitivity of detecting the modified electrical characteristic.

Figure 2:
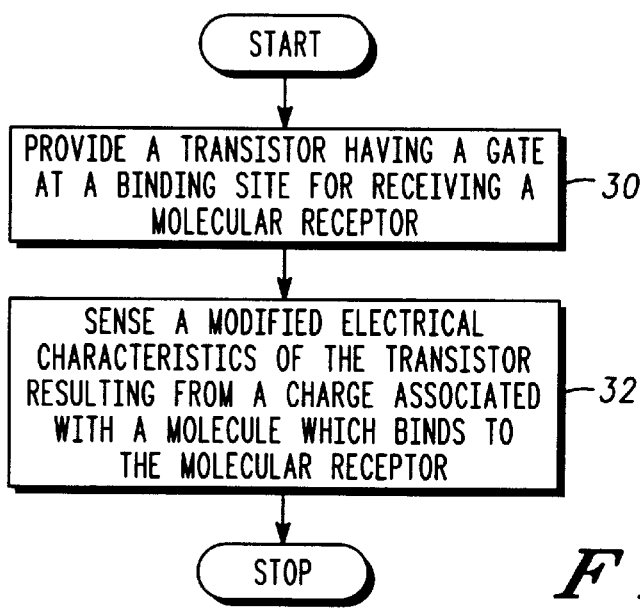
FIG. 2 is a flow chart of an embodiment of a method of sensing a binding of a molecule to a molecular receptor in a molecular detection apparatus.

FIG. 2 is a flow chart of an embodiment of a method of sensing a binding of a molecule to a molecular receptor in a molecular detection apparatus. As indicated by block 30, the method includes a step of providing a transistor having a gate at a binding site in the molecular detection apparatus. This step can be performed by utilizing any of the various embodiments of a molecular detection apparatus as described herein. The molecular receptor is placed at the binding site defined by the gate of the transistor.

As indicated by block 32, the method includes a step of sensing a modified electrical characteristic of the transistor which results when the molecule binds with the molecular receptor. The modified electrical characteristic results from a charge associated with the molecule being coupled to the gate of the transistor.

The step of sensing the modified electrical characteristic of the transistor can be performed in a variety of ways. Two approaches, which reference the apparatus of FIG. 1, are illustrated by the flow charts in FIGS. 3 and 4.

Figure 3:
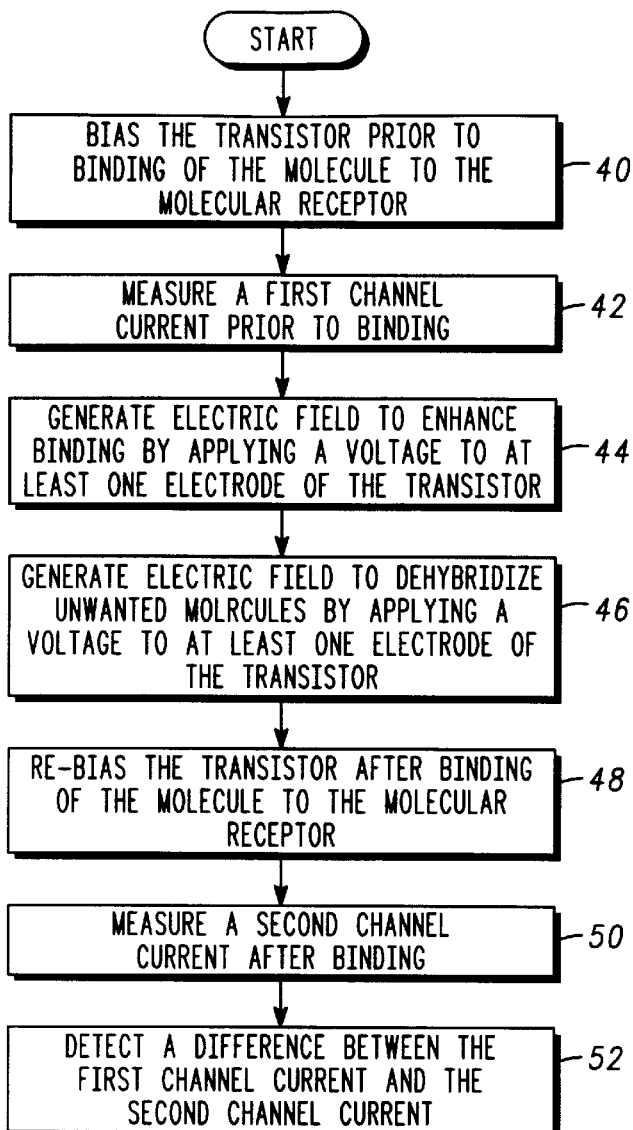
FIG. 3 is a flow chart of an embodiment of a method of sensing a modified electrical characteristic of the transistor.

FIG. 3 is a flow chart of an embodiment of a method of sensing a modified electrical characteristic of the transistor 12. As indicated by block 40, the method includes a step of biasing the transistor 12 in a predetermined manner prior to the binding of the molecule 24 with the molecular receptor 22. Here, a respective, predetermined voltage level is applied to each of the source 16 and the drain 18 of the transistor 12. If the transistor 12 includes the second gate 28, this step optionally includes a step of applying a predetermined voltage level to the second gate 28.

As indicated by block 42, a step of measuring a first channel current between the source 16 and the drain 18 is performed prior to the binding of the molecule 24 with the molecular receptor 22. The first channel current results from the biasing of the transistor 12 performed in the previous step.

After measuring the first channel current, the molecule 24 is allowed to hybridize or bind with the molecular receptor 22. As indicated by block 44, the binding can be field-enhanced by performing a step of applying a first voltage to at least one of the gate 14, the source 16, and the drain 18. The first voltage is selected to generate an electric field which attracts the molecule 24 to the binding site. In a preferred embodiment, substantially all of this electric field is generated by a voltage applied to the gate 14.

After hybridization, an optional step of dehybridizing any unwanted molecules from the binding site can be performed. Specifically, as indicated by block 46, a step of dehybridization can be performed by applying a second voltage to at least one of the gate 14, the source 16, and the drain 18. The second voltage is selected to provide an electric field which repels unwanted molecules from the binding site. The unwanted molecules can include non-bound molecules and partially-bound molecules, for example. Preferably, substantially all of this electric field is generated by a voltage applied to the gate 14.

As indicated by block 48, a step of re-biasing the transistor 12 is performed. Here, the transistor 12 is biased in the same predetermined manner as in the step indicated by block 40.

As indicated by block 50, a step of measuring a second channel current between the source 16 and the drain 18 is performed after the binding of the molecule 24 with the molecular receptor 22. The second channel current results from the biasing of the transistor 12 performed in the previous step.

The modified electrical characteristic is sensed by a step of detecting a difference between the first channel current and the second channel current, indicated by block 52. For example, the modified electrical characteristic may be determined when a difference between the first channel current and the second channel current is beyond a predetermined threshold.

If desired, the voltage applied to the second gate 28 in the biasing steps indicated by blocks 40 and 48 is selected to provide a gain control which improves the sensitivity of detecting a difference between the first channel current and the second channel current.

Figure 4:
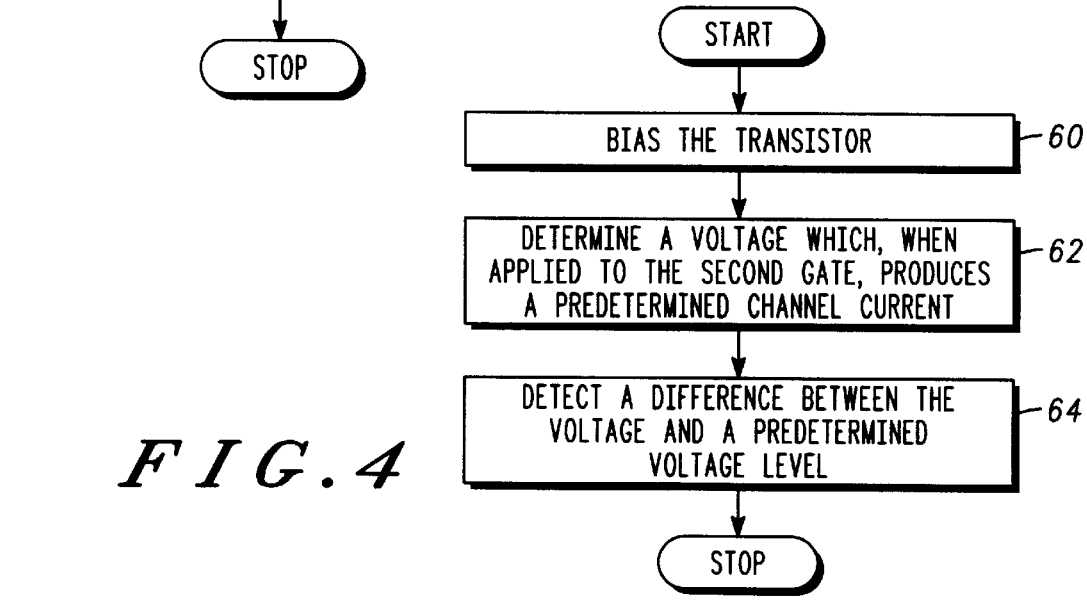
FIG. 4 is a flow chart of another embodiment of a method of sensing a modified electrical characteristic of the transistor.

FIG. 4 is a flow chart of another embodiment of a method of sensing a modified electrical characteristic of the transistor 12. As indicated by block 60, the method includes a step of biasing the transistor 12 in a predetermined manner. Here, a respective, predetermined voltage level is applied to each of the source 16 and the drain 18.

As indicated by block 62, a step of determining a voltage for the second gate 28 to produce a predetermined channel current is performed. The modified electrical characteristic is sensed by a step, indicated by block 64, of detecting a difference between a predetermined voltage level and the voltage determined in the above-described step. The predetermined voltage level can be, for example, a voltage which produces the predetermined channel current before hybridization. Hence, the modified electrical characteristic may be determined when the second gate voltage (post-hybridization) which produces the predetermined channel current is beyond a predetermined threshold.

FIG. 5 is a schematic, block diagram of another embodiment of a molecular detection apparatus in accordance with the present invention. The molecular detection apparatus includes a first transistor 70, which acts as a sensing device, and a second transistor 72 which acts a switching device. The first transistor 70 has a gate 74, a source 76, and a drain 78. The gate 74 is located at a binding site for receiving a molecular receptor. A modified electrical characteristic of the first transistor 70 results when a molecule binds with the molecular receptor.

The second transistor 72 selectively couples and uncouples the gate 74 of the first transistor 70 with a voltage source 80 to selectively generate an electric field at the binding site. In the illustrated embodiment, the second transistor 72 includes a source 82 coupled to the voltage source 80, and a drain 84 coupled to the gate 74 of the first transistor. The second transistor 72 further includes a gate 86 which receives an input signal to selectively control an electrical coupling between the source 82 and the drain 84. Hence, the input signal controls a selective electrical coupling and uncoupling between the voltage source 80 and the gate 74 of the first transistor 70.

The voltage source 80 is applied between the source 82 of the second transistor 72 and a counter electrode 88. The counter electrode 88 is disposed at a location which is distant from the binding site.

To generate an electric field at the binding site, the second transistor 72 is turned-on by applying an appropriate input signal to the gate 86. In response to this input signal, the voltage source 80 becomes electrically coupled to the gate 74 of the first transistor 70. Consequently, an electric field is generated at the gate 74. The polarity and magnitude of the electric field is dependent upon the polarity and magnitude of the voltage source 80. In general, the polarity and magnitude of the voltage source 80 is selected in dependence upon whether a hybridization step, a dehybridization step, or a screening step is to be performed.

To perform a sensing or a detection step, the second transistor 72 is turned-off by applying an appropriate input signal to the gate 86. In response to this input signal, the gate 74 of the first transistor 70 becomes electrically uncoupled from the voltage source 80. Thereafter, any of the herein-described approaches for sensing a modified electrical characteristic of the first transistor 70 can be utilized to sense a molecule bound at the binding site.

FIG. 6 is a schematic, block diagram of yet another embodiment of a molecular detection apparatus. This embodiment includes a first transistor 100, a second transistor 102, a voltage source 104, and a counter electrode 106 interconnected as in FIG. 6. However, the first transistor 100 in this embodiment further includes a back gate 108. The back gate 108 is utilized as a means of gain control and/or active feedback to improve the sensitivity of detecting the modified electrical characteristic of the first transistor 100.

For example, the back gate 108 can be utilized in accordance with the method of FIG. 4 to sense the modified electrical characteristic.

FIG. 7 is a schematic, block diagram of a further embodiment of a molecular detection apparatus in accordance with the present invention. This embodiment utilizes a first sensing transistor 110 and a second sensing transistor 112 coupled to form a differential pair. The first sensing transistor 110 has a gate 114, a source 116, and a drain 118. The second sensing transistor 112 has a gate 120, a source 122, and a drain 124. The source 116 is coupled to the source 122 to form the differential pair.

The gate 114 of the first sensing transistor 110 is located at a first binding site for receiving a first molecular receptor. The gate 120 of the second sensing transistor 112 is located at a second binding site for receiving a second molecular receptor. To perform differential hybridization and sensing thereof, the first binding site and the second binding site receive like molecular receptors.

A first switching transistor 126 includes a gate 128, a source 130, and a drain 132. A voltage source 134 is applied between the source 130 and a counter electrode 136 located distant from the first binding site. The drain 132 is coupled to the gate 114 of the first sensing transistor 110. Based upon an input signal applied to the gate 128, the first switching transistor 126 selectively couples and uncouples the gate 114 of the first sensing transistor 110 with the voltage source 134. As a result, an electric field can be selectively generated at the first binding site.

A second switching transistor 140 includes a gate 142, a source 144, and a drain 146. A voltage source 148 is applied between the source 144 and a counter electrode 150 located distant from the second binding site. It is noted that the counter electrodes 136 and 150 can comprise separate electrodes or can comprise a single electrode.

The drain 146 is coupled to the gate 120 of the second sensing transistor 112. Based upon an input signal applied to the gate 142, the second switching transistor 140 selectively couples and uncouples the gate 120 of the second sensing transistor 112 with the voltage source 148. As a result, an electric field can be selectively generated at the second binding site.

To generate electric fields at the first binding site and the second binding site, the first switching transistor 126 and the second switching transistor 140 are turned-on by applying appropriate input signals to the gates 128 and 142. The first switching transistor 126 and the second switching transistor 140 can be turned-on either substantially simultaneously or sequentially. The polarity and magnitude of the electric fields are dependent upon the polarity and magnitude of the voltage sources 134 and 142.

To enhance a differential hybridization event between the first binding site and the second binding site, the magnitudes of the voltage sources 134 and 142 are selected to differ by a voltage differential. If molecules having an affinity to the molecular receptors at the first binding site and the second binding site are applied to the apparatus, the voltage differential leads to an increased number of molecules bound to molecular receptors at one of the two binding sites.

A binding event can be detected by, first, applying appropriate input signals to the gates 128 and 142 to turn-off the first switching transistor 126 and the second switching transistor 140. As a result, the gates 114 and 120 become uncoupled with the voltage sources 134 and 142. The first switching transistor 126 and the second switching transistor 140 can be turned-off either substantially simultaneously or sequentially.

Next, a difference in a predetermined electrical characteristic between the first sensing transistor 110 and the second sensing transistor 112 is sensed to detect the differential hybridization. The differential hybridization is detected when the difference is beyond a predetermined threshold.

In one embodiment, the differential pair formed by the first sensing transistor 110 and the second sensing transistor 112 is biased to detect a difference in the channel conductance which results from the differential hybridization. The difference in channel conductances causes a difference in channel currents in the differential pair. In general, the differential pair provides a signal, such as a voltage or a current, indicative of a differential hybridization event.

Optionally, the first sensing transistor 110 includes a back gate 152, and the second sensing transistor 112 includes a back gate 154. Here, the differential hybridization event can be detected by detecting a non-zero offset voltage which, when applied between the back gates 152 and 154, produces equal channel currents for the first sensing transistor 110 and the second sensing transistor 112. The differential hybridization event is sensed when the offset voltage is beyond a predetermined threshold.

The embodiment of FIG. 7 can be modified to eliminate the use of the counter electrodes 136 and 150. Such a modification is illustrated in FIG. 8.

Figure 8:
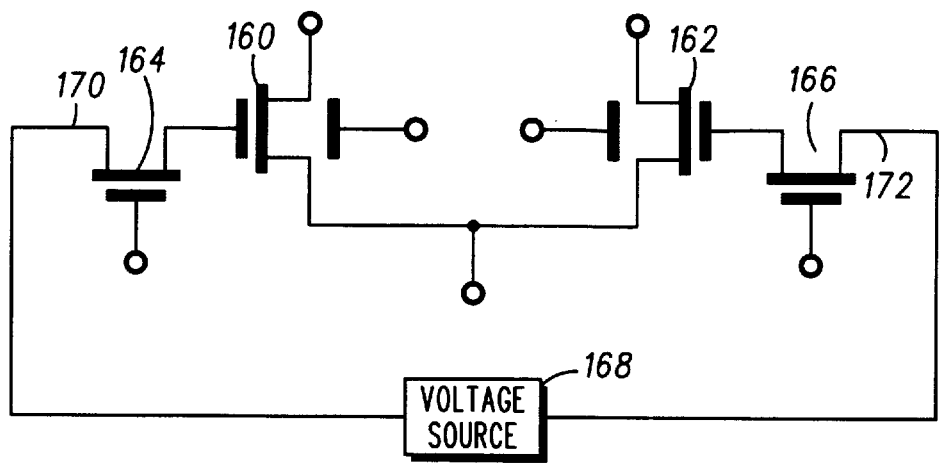
FIG. 8 is a schematic, block diagram of a still further embodiment of the present invention.

FIG. 8 is a schematic, block diagram of a still further embodiment of the present invention. This embodiment includes a first sensing transistor 160, a second sensing transistor 162, a first switching transistor 164, and a second switching transistor 166 as in FIG. 7. However, a voltage source 168 is applied between a source 170 of the first switching transistor 164 and a source 172 of the second switching transistor 166. The magnitude of the voltage generated by the voltage source 168 provides the voltage which leads to an increased number of molecules bound to molecular receptors at one of the two binding sites.

Figure 9:
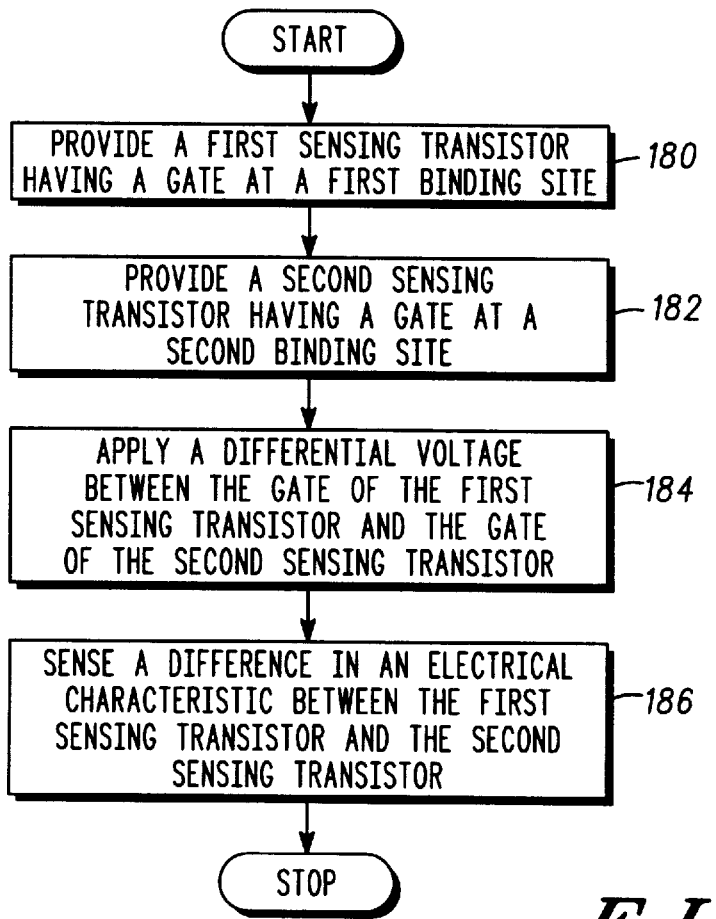
FIG. 9 is a flow chart summarizing steps performed for enhancing and sensing a differential binding event.

FIG. 9 is a flow chart summarizing steps performed for enhancing and sensing a differential binding event. As indicated by block 180, the method includes a step of providing a first sensing transistor having a gate which supports a first binding site. As indicated by block 182, the method includes a step of providing a second sensing transistor having a gate which supports a second binding site. The first binding site and the second binding site receive like molecular receptors.

As indicated by block 184, a step of applying a differential voltage between the gate of the first sensing transistor and the gate of the second sensing transistor is performed to field-enhance the differential binding event. As illustrated in FIGS. 7 and 8, the differential voltage can be applied using either a single voltage source or two voltage sources.

As indicated by block 186, the differential binding event is sensed by a step of sensing a difference in an electrical characteristic between the first sensing transistor and the second sensing transistor. This step can include sensing a difference in channel conductances or channel currents between the first sensing transistor and the second sensing transistor. Alternatively, this step can include a step of detecting a non-zero offset voltage which, when applied to between back gates of the first and second sensing transistors, produces equal channel currents.

Although illustrated in terms of a single molecular receptor at the binding site, it is noted that embodiments of the present invention are typically utilized with a plurality of like molecular receptors located at the binding site. Here, the plurality of like molecular receptors are utilized for detecting a predetermined molecular structure in a sample of target molecules.

Further, it is noted that embodiments of the present invention typically have an array of binding sites for detecting different molecular structures within a sample of target molecules. Here, each binding site has a sensing transistor and, optionally, a switching transistor associated therewith. The plurality of transistors which form such a molecular detection apparatus can all be integrated with a single substrate using TFT or MOSFET technologies, for example.

It is also noted that any suitable switching device capable of selectively coupling and uncoupling a pair of terminals based upon a signal received at a control input can be substituted for any of the switching transistors described herein.

Thus, there has been described herein a concept, as well as several embodiments including preferred embodiments of a transistor-based molecular detection apparatus and method.

Because the various embodiments of the present invention detect a binding event by sensing a charge associated with a target molecule, they provide a significant improvement in that a transistor integrated in the molecular detection apparatus can be utilized to electronically detect the target molecule. To improve detection, the charge associated with the target molecule can be enhanced by attaching a charged bead to the target molecule.

Additionally, the various embodiments of the present invention as herein-described utilize the gate in the transistor to perform field-assisted hybridization and dehybridization.

Further, a pair of transistors can be utilized to enhance and sense a differential hybridization event. This configuration is beneficial in eliminating the requirement of a counter electrode.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. A molecular detection apparatus comprising:
 a first transistor having a first gate;
 a first molecular receptor proximate to the first gate;
 a second transistor having a second gate; and
 a second molecular receptor proximate to the second gate;
 wherein a differential voltage is applied between the first gate and the second gate to enhance a binding difference between the first molecular receptor and the second molecular receptor.

2. The molecular detection apparatus of claim 1 further comprising:
 a counter electrode to electrically couple to a sample;
 a first voltage source to apply a first voltage between the first gate and the counter electrode; and
 a second voltage source to apply a second voltage between the second gate and the counter electrode;
 wherein the first voltage and the second voltage differ by the differential voltage.

3. The molecular detection apparatus of claim 1 further comprising a voltage source to apply the differential voltage between the first gate and the second gate without a counter electrode.

4. The molecular detection apparatus of claim 1 wherein the first transistor includes a third gate, wherein the second transistor includes a fourth gate, and wherein a non-zero offset voltage is applied between the third gate and the fourth gate.

5. The molecular detection apparatus of claim 4 wherein the third gate is a back gate of the first transistor, and wherein the fourth gate is a back gate of the second transistor.

6. The molecular detection apparatus of claim 4 wherein the non-zero offset voltage produces a first current in the first transistor and a second current in the second transistor, wherein the first current is equal to the second current.

7. The molecular detection apparatus of claim 1 wherein the first molecular receptor is receptive to a chain of a plurality of nucleotides.

8. The molecular detection apparatus of claim 1 wherein the first molecular receptor is receptive to a DNA molecule.

9. The molecular detection apparatus of claim 1 wherein the first transistor includes a first source, wherein the second transistor includes a second source, and wherein the first source is electrically coupled to the second source.

10. The molecular detection apparatus of claim 1 wherein the first molecular receptor and the second molecular receptor include like molecular receptors.

11. A molecular detection method comprising the steps of:
providing a sample of molecules;
providing a first transistor having a first gate proximate to a first molecular receptor;
providing a second transistor having a second gate proximate to a second molecular receptor;
applying a differential voltage between the first gate and the second gate to enhance a difference in binding of the sample between the first molecular receptor and the second molecular receptor; and
sensing the difference in binding of the sample between the first molecular receptor and the second molecular receptor based upon an electrical characteristic of at least one of the first transistor and the second transistor.

12. The molecular detection method of claim 11 wherein the step of applying the differential voltage comprises steps of:
providing a counter electrode electrically coupled to the sample;
applying a first voltage between the first gate and the counter electrode;
applying a second voltage between the second gate and the counter electrode; and
wherein the first voltage and the second voltage differ by the differential voltage.

13. The molecular detection method of claim 11 wherein the differential voltage is applied between the first gate and the second gate without a counter electrode.

14. The molecular detection method of claim 11 wherein the first transistor includes a third gate, wherein the second transistor includes a fourth gate, the molecular detection method further comprising the step of applying a non-zero offset voltage between the third gate and the fourth gate.

15. The molecular detection method of claim 14 wherein the third gate is a back gate of the first transistor, and wherein the fourth gate is a back gate of the second transistor.

16. The molecular detection method of claim 14 wherein the non-zero offset voltage produces a first current in the first transistor and a second current in the second transistor, wherein the first current is equal to the second current.

17. The molecular detection method of claim 14 wherein the step of sensing binding of the sample includes detecting that the non-zero offset voltage is beyond a threshold.

18. The molecular detection method of claim 11 wherein the first molecular receptor is receptive to a chain of a plurality of nucleotides.

19. The molecular detection method of claim 11 wherein the first molecular receptor is receptive to a DNA molecule.

20. The molecular detection method of claim 11 wherein the first transistor includes a first source, wherein the second transistor includes a second source, and wherein the first source is electrically coupled to the second source.

21. The molecular detection method of claim 11 wherein the first molecular receptor and the second molecular receptor include like molecular receptors.

22. The molecular detection method of claim 11 wherein the step of sensing binding of the sample includes sensing a difference in a first electrical characteristic of the first transistor and a second electrical characteristic of the second transistor.

23. The molecular detection method of claim 22 wherein the first electrical characteristic includes a first current in the first transistor, and wherein the second electrical characteristic includes a second current in the second transistor.

24. The molecular detection method of claim 23 wherein the first current includes a first channel current and wherein the second current includes a second channel current.

25. The molecular detection method of claim 22 wherein the first electrical characteristic includes a first conductance in the first transistor, and wherein the second electrical characteristic includes a second conductance in the second transistor.

26. The molecular detection method of claim 25 wherein the first conductance includes a first channel conductance and wherein the second conductance includes a second channel conductance.

27. The molecular detection apparatus of claim 1 wherein the first transistor includes a first source, wherein the second transistor includes a second source, and wherein the first source is electrically coupled directly to the second source.

28. The molecular detection method of claim 11 wherein the first transistor includes a first source, wherein the second transistor includes a second source, and wherein the first source is electrically coupled directly to the second source.

* * * * *